United States Patent [19]

Tsuji et al.

[11] Patent Number: 5,723,637
[45] Date of Patent: Mar. 3, 1998

[54] PROCESS FOR PRODUCING PROPYLENE OXIDE

[75] Inventors: Junpei Tsuji; Kenshi Uchida; Noriaki Oku; Mitsuhisa Tamura; Masaru Ishino, all of Chiba, Japan

[73] Assignee: Sumitomo Chemical Company, Limited, Osaka, Japan

[21] Appl. No.: 754,125

[22] Filed: Nov. 22, 1996

[30] Foreign Application Priority Data

Dec. 6, 1995 [JP] Japan .................. 7-317841
Jun. 7, 1996 [JP] Japan .................. 8-145493

[51] Int. Cl.$^6$ ............................. C07D 301/19
[52] U.S. Cl. ............................. 549/529
[58] Field of Search ..................... 549/529

[56] References Cited

U.S. PATENT DOCUMENTS 2,829,173  11/1958  Shiffler et al. ............ 260/610
3,923,843  12/1975  Wulff ..................... 549/529

FOREIGN PATENT DOCUMENTS 50-30049   9/1975   Japan .
54-40526   2/1979   Japan .
54-40525   12/1979  Japan .
56-35941   8/1981   Japan .
9500055    1/1997   Japan .

*Primary Examiner*—Frederick Krass
*Attorney, Agent, or Firm*—Sughrue, Mion, Zinn, Macpeak & Seas, PLLC

[57] ABSTRACT

A process for producing propylene oxide which comprises reacting a raw material solution which is a solution of ethylbenzene hydroperoxide in ethylbenzene obtained by liquid phase autoxidation of ethylbenzene with propylene in the presence of a Ti-containing solid catalyst to give propylene oxide, said raw material solution being a solution prepared by washing a solution of ethylbenzene hydroperoxide in ethylbenzene obtained by liquid phase autoxidation of ethylbenzene with an aqueous alkali solution to bring a lactic acid concentration to 5 ppm by weight or less.

8 Claims, No Drawings

PROCESS FOR PRODUCING PROPYLENE OXIDE

BACKGROUND OF THE INVENTION

1. Field of the Invention

The present invention relates to a process for producing propylene oxide. More precisely, the present invention relates to a process for producing propylene oxide which enables to suppress depression of activity of the catalyst used in the reaction with the passage of time.

2. Background Information

Propylene oxide is an industrial chemical used as a raw material for producing, for example, polyurethane.

A method is known for converting an olefin compound into an oxirane compound by reacting an olefin compound with ethylbenzene hydroperoxide in the presence of a Ti-containing solid catalyst (see JP-B-56-35941, JP-B-54-40525, JP-B-54-40526, JP-B-50-30049). It has been known, however, that an industrially undesirable phenomenon, depression of activity of the Ti-containing solid catalyst with the passage of time, occurs when propylene oxide is produced by reacting an impurity-containing ethylbenzene hydroperoxide, such as one produced industrially, with propylene in the presence of the Ti-containing solid catalyst.

As the result of extensive studies for suppressing or preventing deactivation of the catalyst, the present inventors have found that the deactivation can be suppressed or prevented by conducting the epoxidation reaction using a raw material solution which is prepared by washing a solution of ethylbenzene hydroperoxide in ethylbenzene with an aqueous alkali solution to bring a lactic acid concentration to 5 ppm by weight or less, which fact led them to the present invention.

SUMMARY OF THE INVENTION

Thus, the present invention relates to a process for producing propylene oxide which comprises reacting a raw material solution which is a solution of ethylbenzene hydroperoxide in ethylbenzene obtained by liquid phase autoxidation of ethylbenzene with propylene in the presence of a Ti-containing solid catalyst to give propylene oxide, said raw material solution being a solution prepared by washing a solution of ethylbenzene hydroperoxide in ethylbenzene obtained by liquid phase autoxidation of ethylbenzene with an aqueous alkali solution to bring a lactic acid concentration to 5 ppm by weight or less.

DETAILED DESCRIPTION OF THE INVENTION

The raw material for the present invention is a solution of ethylbenzene hydroperoxide in ethylbenzene obtained by liquid phase autoxidation of ethylbenzene.

Liquid phase autoxidation of ethylbenzene (hereinafter, abbreviated as EB) is usually effected with molecular oxygen at 50°–150° C. In order to maintain the selectivity to ethylbenzene hydroperoxide (hereinafter, abbreviated as EBHP) at a high level, the conversion of EB is kept at a low level. Therefore, the EBHP concentration in the oxidation reaction solution is usually about 5–15% by weight. Generally, the oxidation reaction solution is subjected to a concentration step partially removing low temperature boiling fractions such as EB to enhance EBHP concentration before using in the epoxidation reaction with propylene.

It has been found, however, that substances acting as a catalyst poison for Ti-containing solid catalyst exist in the oxidation reaction and is not removed in the concentration step. Among these substances, the most poisonous one is lactic acid, which may exist, depending on the oxidation conditions, in a concentration of several tens ppm during the oxidation reaction. Further, the raw material contains organic acids other than lactic acid and these organic acids may also adversely affect the catalytic activity. Therefore, it is necessary to remove catalyst poisons, particularly lactic acid, in the EBHP raw material solution, and for this reason, washing with an aqueous alkali solution is required.

When the washing with an aqueous alkali solution is conducted, the EBHP concentration in the raw material solution is preferably 10–25% by weight and more preferably 12–20% by weight. An EBHP concentration lower than the above level may be economically undesirable due to a large rate of loss of EBHP in waste alkali and a large washing apparatus required. Also, an EBHP concentration higher than the above level may result in insufficient phase separation in the alkali washing lowering the rate of removal of catalyst poisons including lactic acid. An EBHP solution having a concentration within the above range can be easily obtained by concentration through appropriate extent of distillation of the oxidation reaction solution.

Suitable alkali sources in the aqueous alkali solution for use in washing include alkali metal hydroxides, alkali metal carbonates, alkali metal hydrogen carbonates, for example, NaOH, KOH, $Na_2CO_3$, $K_2CO_3$, $NaHCO_3$, $KHCO_3$ and the like, ammonia, amines and the like. Because of inexpensiveness and easy availability in the industrial market, NaOH and $Na_2CO_3$ are particularly preferred. The concentration of the aqueous alkali solution is preferably 0.01–30% by weight, more preferably 0.05–20% by weight, further preferably 0.05–10% by weight and most preferably 0.1–10% by weight.

The volume ratio (o/w) of the solution of the EBHP raw material oil to the fresh aqueous alkali solution is preferably 1000/1–1/1, more preferably 200/1–2/1 and most preferably 100/1–10/1. A too high concentration of alkali or too low o/w may be economically undesirable due to increase in the amount of alkali to be used or increase in the amount of waste water or of alkali in waste water. Also, a too low concentration of alkali or too high o/w may result in insufficient removal of catalyst poisons, including lactic acid, in the EBHP raw material oil.

The alkali washing can be effected by appropriately mixing the above described EBHP raw material solution and the aqueous alkali solution, settling the mixture to form separate phases and recovering the oily phase containing EBHP. The temperature during washing and settling is preferably 0°–100° C. and more preferably 30°–80° C. If the temperature is too high, undesirable side reactions such as heat decomposition of EBHP may occur and if the temperature is too low, energy required for cooling may be excessive. The period for mixing and settling is not particularly limited insofar as it provides necessary and sufficient mixing and settling and usually is about 1–100 minutes. The alkali washing can be conducted either by batch operation or in continuous operation. A part of the waste aqueous alkali from the washing step may be recycled to use in admixture with the fresh aqueous alkali solution.

The lactic acid concentration in the EBHP raw material oil obtained after the alkali washing should be 5 ppm by weight or less. It is preferred to control the concentration to 1 ppm by weight or less by adjusting the alkali washing to the above described preferred range.

The oily phase obtained after the alkali washing may further be washed with water. In this case, the conditions (o/w ratio, temperature, period etc.) for the water washing may be similar to those for the alkali washing.

It is preferred that the above described washing with the aqueous alkali solution is conducted after increasing the EBHP concentration in the reaction solution resulted from oxidation of ethylbenzene preferably up to 10–25% by weight and more preferably to 12–20% by weight. Further, it is preferred to subject the oily phase obtained by washing with the aqueous alkali to concentration by distillation. By such concentration after washing, water dissolved in the raw material during washing can be azeotropically removed with EB.

When the raw material solution is used after the alkali washing and water washing or concentration, for example by distillation, the lactic acid concentration in the EBHP raw material oil should be 5 ppm by weight or less and preferably 1 ppm by weight or less.

The raw material also contains organic acids other than lactic acid, the amount of which is usually about 0.01–0.5% by weight. Said organic acids include formic acid, acetic acid, propionic acid, benzoic acid and the like. Since these organic acids may adversely affect the catalytic activity, it is desirable to use the raw material having a content of the organic acids including lactic acid in the solution to be charged (propylene+a solution of EBHP in EB) preferably of 2 µmol/g or less and more preferably of 1 µmol/g or less. The content of the organic acids in the solution to be charged can be easily determined by ion chromatography, liquid chromatography or the like.

When much amount of water is contained in the raw material, the catalytic activity in the epoxidation step may be remarkably decreased and the produced propylene oxide (hereinafter, abbreviated as PO) may react with it resulting in decrease in yield. It is desirable that the water content in the raw material is one which allows to suppress the concentration of propylene glycol as the side product in the product to a level preferably of 10 µmol/g or less and more preferably of 5 µmol/g or less. The concentration of propylene glycol in the product can be easily determined by gas chromatography.

The raw material solution obtained as above may be concentrated in order to be used in the subsequent epoxidation step as a solution having a preferred EBHP concentration.

Next, the epoxidation reaction is illustrated.

The catalyst used in the present invention is a Ti-containing solid catalyst including, for example, Ti compounds carried on various carriers, complexes with other oxides formed by co-precipitation or sol-gel process, Ti-containing zeolite oxides and the like. Catalysts containing titanium chemically bound with solid silica and/or inorganic silicate, so-called Ti-silica catalysts, are preferably used. These can be prepared by the known processes described below (see JP-B-56-35941, JP-B-54-40525, JP-B-54-40526, JP-B-50-30049).

For example, silica gel which is a solid silica, a titanium compound such as tetraisopropyl titanate, tetraethyl titanate or the like, and an additive such as acetylacetone, if necessary, are added to a solvent such as isopropanol, ethanol or the like. They are mixed at room temperature and the solids are separated by filtration. The solids are washed with a solvent such as isopropanol, ethanol or the like and dried. The dried solids are calcined at about 400°–900° C. for about 1–18 hours. The solids after calcination are heated with agitation in a silylating agent such as hexamethyldisilazane or the like and a solvent such as toluene at about 50°–300° C. for about 0.5–5 hours and solids are separated by filtration. Then the solids are washed with a solvent such as toluene or the like and dried under vacuum to give the catalyst used in the present invention.

The epoxidation reaction can be carried out by reacting the EBHP raw material solution after treatment by washing with the aqueous alkali solution and propylene in the presence of the catalyst as described above.

In the epoxidation reaction, the concentration of EBHP in the EBHP raw material solution is preferably 10–50% by weight and more preferably 15–40% by weight. It is preferred to use a EBHP raw material solution treated with an aqueous alkali solution and concentrated.

If the concentration is too high, undesirable side reactions such as heat decomposition of EBHP may increase resulting in decrease in selectivity of the reaction and if the concentration is too low, too much amount of the catalyst or too large reaction vessel is required due to lowered reaction rate or productivity.

The EBHP raw material solution of concentration within such range can be obtained by distilling the washed oil to remove a part of the low temperature boiling fractions such as EB as described above. The concentration of lactic acid in the EBHP raw material solution should be 5 ppm by weight or less and is preferably 1 ppm by weight or less in order to minimize deactivation of the catalyst.

The molar ratio of propylene to EBHP used in the epoxidation reaction is preferably 1:1–20:1.

If the amount of propylene is too small, the reaction rate and the selectivity of the reaction may decrease and if the amount is too large, the productivity may be lowered or excess energy for recycling unreacted propylene may be required.

It is preferred to remove water in the reaction system because it has an action of accelerating the side reaction. If water exists in the reaction system, propylene glycol is formed as the side product from the reaction of propylene and ethylbenzene hydroperoxide. The means for removing water in the reaction system includes dehydrating agent such as molecular sieve, silica gel, orthoformic acid esters, dicyclohexyl carbodiimide or the like, distillation and the like.

It is preferred to conduct the reaction by continuous process, including a process in which a catalyst in the form of solid pellets is enclosed in a reaction tube and the EBHP raw material solution and propylene are passed through the tube, a process in which the reaction is carried out by a slurry reaction using powdered catalyst and the like. The reaction temperature is preferably 0°–200° C., more preferably 25°–200° C. and most preferably 30°–150° C. At a lower temperature, the reaction may be slow and at a higher temperature, the selectivity of the reaction may be low. The pressure in the reaction system is preferably 1–100 atm and more preferably 10–50 atm. Under a lower pressure, the reaction may be slow and for a higher pressure, an excessive cost may be required for the apparatus.

The reaction period is about 0.5–5 hours when the reaction is carried out by the batch system and about 0.5–20 hour$^{-1}$ in the liquid hourly space velocity when the reaction is carried out by the flow system. Ethylbenzene hydroperoxide is usually subjected to the epoxidation reaction in the form of a solution in ethylbenzene used as the raw material and solvent in its production. The solution in ethylbenzene may contain side products formed in the reaction. A second solvent may be used in the reaction as a diluent. The second solvent includes aromatic compounds such as benzene, toluene, chlorobenzene, bromobenzene, orthodichlorobenzene and the like and aliphatic compounds such as octane, decane, dodecane and the like. Also, propylene as the reactant may be used in excess for substituting a part of the solvent.

Unreacted propylene in the epoxidation reaction solution can be recycled to the reaction system after separating by distillation. Final removal of propylene from the reaction solution after removing major part of the unreacted propylene may be carried out by usual operation such as distillation, washing or the like.

EXAMPLES

Reference Example 1 [Preparation of catalyst]

Commercial silica gel (10–40 mesh; surface area: 300 m$^2$/g; average pore size: 10 nm; 50 g), tetraisopropyl titanate (1.1 g), acetylacetone (0.82 g) and isopropanol (200 ml) were mixed, the mixture was stirred at room temperature for 30 minutes and filtered. Solid portion was immersed in isopropanol (50 ml), agitated for washing and the liquid was removed by filtration. This operation was repeated three times. Then the solid portion was dried under a nitrogen stream at 500° C. for 2 hours and further calcined under an air stream at 600° C. for 4 hours.

The obtained substance (10 g), hexamethyldisilazane (4 g) and toluene (50 g) were mixed and the mixture was heated with stirring under pressure at 200° C. for 1 hour. The liquid was removed from the mixture by filtration. The solid portion was washed with toluene (50 g) and dried under vacuum (120° C.; 10 mmHg; 3 hours) to give the catalyst.

Example 1

Alkali Washing of EBHP Solution

An EBHP solution (15% by weight; 3000 g) and a sodium hydroxide solution (0.5% by weight; 1000 g) were mixed and the mixture was stirred at 60° C. for 15 minutes and left to stand at the same temperature for 15 minutes, followed by phase separation. The oily phase was mixed with 1000 g of water and the mixture was stirred at 60° C. for 15 minutes and left to stand at the same temperature for 15 minutes. The obtained oily layer was concentrated at 60° C. under 50 mmHg to give an EBHP solution having a concentration of 35% by weight.

Reaction

The epoxidation reaction was conducted in a fixed bed flow reactor using a catalyst prepared according to the method of Reference Example 1 (Ti content: 0.3% by weight), an EBHP solution (containing 35% by weight of EBHP, 58% by weight of EB and 0.3 ppm by weight of lactic acid) obtained by the above described washing process and propylene. The reaction was carried out under conditions of propylene/EBHP=12, LHSV=12, heater temperature of 99° C. and reaction pressure of 40 kg/cm$^2$. The results are shown in Table 1.

Comparative Example 1

The reaction was repeated under the same conditions as those in Example 1 except that an EBHP solution without alkali washing was used. The results are shown in Table 1.

Example 2

The epoxidation reaction was conducted in a fixed bed flow reactor using a catalyst prepared according to the method of Reference Example 1 (Ti content: 0.3% by weight), an EBHP solution (containing 35% by weight of EBHP, 58% by weight of EB and 3.1 ppm by weight of lactic acid) obtained by a washing process similar to that described in Example 1 and propylene. The reaction was carried out under conditions of propylene/EBHP=11, LHSV=12, heater temperature of 65° C. and reaction pressure of 40 kg/cm$^2$. The results are shown in Table 2.

Comparative Example 2

The reaction was repeated under the same conditions as those in Example 1 except that an alkali-washed EBHP solution obtained in Example 1 and enriched With. 100 ppm by weight of lactic acid was used as the raw material. The results are shown in Table 2.

Example 3

An EBHP solution (34.8% by weight; solvent: ethylbenzene; 2000 g) and an aqueous sodium carbonate solution (10% by weight; 200 g) were mixed and the mixture was stirred, followed by phase separation. The oily phase was washed again with an aqueous sodium carbonate solution (10% by weight; 200 g). The oily phase was washed 11 times with 200 g of water and dried with silica gel to give an EBHP solution (32.7% by weight).

A catalyst prepared according to the method of Reference Example 1(Ti content based on charging amount: 0.37% by weight; 4 g), an EBHP solution (60 g) obtained by the above described washing process and propylene (75 g) were charged in an autoclave and the reaction was conducted at 120° C. for 1 hour. After the reaction was terminated, the catalyst was recovered by filtration and washed with ethylbenzene. Then the same reaction was repeated using the recovered and washed catalyst. The reaction was repeated three times in this manner. The concentration of lactic acid in the EBHP solution was 1.9 ppm by weight. The concentration of organic acids including lactic acid in the charged solution (propylene+EBHP solution) was 0.2 µmol/g. The concentration of propylene glycol in the reaction mixture was 4 µmol/g. The results are shown in Table 1.

Comparative Example 3

The reaction was repeated three times under the same conditions as those in Example 3 except that an EBHP solution without alkali washing was used. The concentration of lactic acid in the EBHP solution was 47 ppm by weight. The concentration of organic acids including lactic acid in the charged solution (propylene+EBHP solution) was 7.6 µmol/g. The concentration of propylene glycol in the reaction mixture was 3 µmol/g. The results are shown in Table 3.

From the results, it can be understood that almost no decrease in catalytic activity with the passage of time was observed in Examples 1, 2 and 3 which meet the requirements under the present invention. On the other hand, remarkable decrease in catalytic activity was observed in Comparative Examples 1, 2 and 3 which fails to meet the requirements under the present invention.

TABLE 1

|  | Example 1 | | Comparative Example 1 | |
| --- | --- | --- | --- | --- |
| EBHP solution for reaction | | | | |
| Kind*1 | A | — | B | — |
| Lactic acid concentration, ppm by wt. | 0.3 | — | 68 | — |
| Reaction period, hr | 1 | 8 | 1 | 7 |
| Results of reaction Conversion of EBHP, % | 99.2 | 99.0 | 99.8 | 77.9 |

TABLE 2

|  | Example 2 |  | Comparative Example 2 |  |
|---|---|---|---|---|
| EBHP solution for reaction |  |  |  |  |
| Kind*1 | C | — | D | — |
| Lactic acid concentration, ppm by wt. | 3.1 | — | 103 | — |
| Reaction period, hr | 1 | 3 | 1 | 3 |
| Results of reaction Conversion of EBHP, % | 88.2 | 87.9 | 86.9 | 78.5 |

*1 EBHP solution for reaction, Kind
A and C: solution washed with alkali followed by concentration
B: solution without alkali-washing
D: solution washed with alkali followed by concentration and then lactic acid was added into the solution

TABLE 3

|  | Example 3 | Comparative Example 3 |
|---|---|---|
| Concentration |  |  |
| Lactic acid, ppm by wt. *1 | 1.9 | 47 |
| Organic acids, μmol/g *2 | 0.2 | 7.6 |
| PG μmol/g *3 | 4 | 3 |
| Relative ratio of reaction Rate *4 |  |  |
| First time | 1.00 | 1.00 |
| Second time | 0.95 | 0.91 |
| Third time | 1.00 | 0.73 |

*1 Concentration in the EBHP solution
*2 Concentration in the charged solution (propylene +EBHP solution)
*3 PG: propylene glycol. Concentration in the reaction mixture.
*4 Relative ratio of reaction rate: relative value when the reaction rate in the first time is taken as 1

What is claimed is:

1. A process for producing propylene oxide which comprises reacting a raw material solution, which is a solution of ethylbenzene hydroperoxide in ethylbenzene obtained by liquid phase autoxidation of ethylbenzene, with propylene in the presence of a Ti-containing solid catalyst to give propylene oxide, said raw material solution being a solution prepared by washing a solution of ethylbenzene hydroperoxide in ethylbenzene, obtained by liquid phase autoxidation of ethylbenzene, with an aqueous alkali solution to bring the lactic acid concentration to 5 ppm by weight or less.

2. The process according to claim 1, in which the raw material solution is a solution having a lactic acid concentration of 1 ppm by weight or less.

3. The process according to claim 1, in which the raw material solution is a solution containing 10–25% by weight of ethylbenzene hydroperoxide in ethylbenzene washed with an aqueous alkali solution.

4. The process according to claim 1, in which the alkali is sodium hydroxide or sodium carbonate.

5. The process according to claim 1, in which the aqueous alkali solution has an alkali concentration of 0.01–30% by weight.

6. The process according to claim 1, in which the volume ratio (o/w) of the solution of ethylbenzene hydroperoxide in ethylbenzene to the aqueous alkali solution is 100/1–10/1.

7. The process according to claim 1, in which the raw material solution is a solution obtained by washing with an aqueous alkali solution and distilling and has an ethylbenzene hydroperoxide concentration of 1–50% by weight and a lactic acid concentration of 5 ppm by weight or less.

8. The process according to claim 1, wherein said Ti-containing solid catalyst is a Ti-silica catalyst.

* * * * *